United States Patent [19]

Farris

[11] Patent Number: 5,370,626
[45] Date of Patent: Dec. 6, 1994

[54] PLUNGERLESS SYRINGE

[76] Inventor: Barry Farris, P.O. Box 1990, Pollock Pines, Calif. 95726

[21] Appl. No.: 97,095

[22] Filed: Jul. 26, 1993

Related U.S. Application Data

[63] Continuation of Ser. No. 755,521, Sep. 11, 1991, abandoned, which is a continuation-in-part of Ser. No. 584,808, Sep. 18, 1990, Pat. No. 5,102,398.

[51] Int. Cl.$^5$ ............................................. A61M 5/00
[52] U.S. Cl. ................................ 604/187; 604/212; 604/217; 604/408; 222/94
[58] Field of Search ............... 604/48, 49, 187, 190, 604/191, 212-217, 403, 410; 222/94, 96, 129, 130

[56] References Cited

U.S. PATENT DOCUMENTS

| | | | |
|---|---|---|---|
| 1,762,430 | 8/1929 | Tokita . | |
| 2,667,165 | 1/1954 | Smith | 604/216 X |
| 2,744,527 | 5/1956 | Barret et al. | 604/215 X |
| 2,744,528 | 5/1956 | Barrett et al. . | |
| 2,748,770 | 6/1956 | Moeck . | |
| 2,768,623 | 10/1956 | Marchand . | |
| 2,911,972 | 11/1959 | Elinger . | |
| 3,078,847 | 2/1963 | Wandell et al. | 604/410 X |
| 3,089,489 | 5/1963 | Dunmire . | |
| 3,335,914 | 8/1967 | Strazdins et al. | 222/107 |
| 3,340,869 | 9/1967 | Bane | 604/216 X |
| 3,557,788 | 1/1971 | Swartz . | |
| 3,712,295 | 1/1973 | Kline . | |
| 3,736,933 | 6/1973 | Szabo | 604/200 |
| 4,018,222 | 4/1977 | McAleer et al. . | |
| 4,130,117 | 12/1978 | Van Eck . | |
| 4,168,032 | 9/1979 | Sneider | 239/327 |
| 4,282,986 | 8/1981 | af Ekenstam et al. | 222/1 |
| 4,357,937 | 11/1982 | Burrell, Jr. et al. | 604/183 |
| 4,411,656 | 10/1983 | Cornett, III | 604/212 |
| 4,548,601 | 10/1985 | Lary | 604/204 |
| 4,610,670 | 9/1986 | Spencer | 604/29 |
| 4,753,638 | 6/1988 | Peters | 604/212 |
| 4,955,871 | 9/1990 | Thomas | 604/217 |
| 4,994,039 | 2/1991 | Mattson | 604/408 |
| 5,102,398 | 4/1992 | Farris | 604/212 |
| 5,222,950 | 6/1993 | Eisenberg | 604/408 |

FOREIGN PATENT DOCUMENTS

| | | | |
|---|---|---|---|
| 0278032 | 12/1965 | Australia | 604/217 |
| 2058585 | 5/1971 | France | 604/212 |
| 0446819 | 1/1928 | Germany | 604/212 |
| 0556491 | 8/1932 | Germany | 604/212 |
| 3827335 | 2/1990 | Germany | 604/217 |

Primary Examiner—C. Fred Rosenbaum
Assistant Examiner—V. Alexander
Attorney, Agent, or Firm—Bernhard Kreten

[57] ABSTRACT

A hollow, molded, disposable, plastic syringe is provided with an air trap chamber in fluid communication with a collapsible container portion. An umbilical passage connects the container to the chamber. With the air trap chamber extending upwardly from the container portion, air is trapped in the chamber. The chamber is then removed by sealing the umbilical passage shut and severing the passage between the seal and the chamber. The syringe is then useable without any air contained in the container. The container is shaped to facilitate ejection of an accurate dose without injecting too little or too much of the contained liquid.

31 Claims, 2 Drawing Sheets

PLUNGERLESS SYRINGE

This application is a continuation of U.S. patent application Ser. No. 07/755,521, filed Sep. 11, 1991, now abandoned, which is a continutation-in-part of U.S. patent application Ser. No. 07/584,808, filed Sep. 18, 1990, now issued U.S. Pat. No. 5,102,398.

FIELD OF THE INVENTION

The following invention relates generally to medical devices for the injection of fluids. More particularly, the invention relates to a plungerless syringe having means for preventing air from being injected into a patient.

BACKGROUND OF THE INVENTION

Every day large numbers of syringes are utilized in dispensing fluids. Still the primary device utilized for these injections is a small cylindrical container or tube, and a plunger piston manually moved within the tube to eject liquid through an outlet at one end of the tube that is connected to a cannula or tubular needle. Some of such syringes are reutilized with proper sterilization in between uses.

A variation of the foregoing, which is in widespread use, is to position a sealed cartridge into a syringe-like holder, and a piston rod or actuator carried by the holder depresses a piston in the cartridge to eject fluid out of a needle attached to the cartridge. The tube and the needle are conveniently disposable; however, it is somewhat cumbersome to remove the cartridges and there is a risk of the operator being stuck with the needle during the removal process.

The following patents reflect the state of the art of which applicant is aware and are included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| INVENTOR | PATENT NO. | ISSUE DATE |
| --- | --- | --- |
| Viviez | 470,700 (France) | April 7, 1914 |
| Tokita | 1,762,430 | August 31, 1929 |
| Wirth | GB557,400 | November 18, 1943 |
| Barrett, et al. | 2,744,528 | May 8, 1956 |
| Moeck | 2,748,770 | June 5, 1956 |
| Marchand | 2,768,623 | October 30, 1956 |
| Elinger | 2,911,972 | November, 10, 1959 |
| Dunmire | 3,089,489 | May 14, 1963 |
| Strazdins, et al. | 3,335,914 | August 15, 1967 |
| Bane | 3,340,869 | September 12, 1967 |
| Swartz | 3,557,788 | March 8, 1968 |
| Kline | 3,712,295 | January 23, 1973 |
| Szabo | 3,736,933 | June 5, 1973 |
| McAleer, et al. | 4,018,222 | April 19, 1977 |
| Van Eck | 4,130,117 | December 19, 1978 |
| Sneider | 4,168,032 | September 18, 1979 |
| af Ekenstam, et al. | 4,282,986 | August 11, 1981 |
| Cornett, III | 4,411,656 | October 25, 1983 |
| Lary | 4,548,601 | October 22, 1985 |
| Peters | 4,753,638 | June 28, 1988 |

In general, these patents disclose a variety of small, plastic containers or ampoules which can be squeezed to eject the container contents through an outlet adapted to be connected to a needle to be inserted into a patient. Although these devices have been available for some time, they do not seem to be widely used. One reason for this may be that such plungerless syringes are deemed to present a possible safety hazard to the patient because of the possibility of air or gas being injected into the patient.

During any process of filling a plungerless syringe with a liquid, there is inevitably some air or other gas which remains trapped in the container. Likewise there is usually gas within a plunger-type syringe. With a syringe having a plunger, the common technique of removing the gas before injecting the liquid into the container is to point the needle of the syringe upwardly causing the gas to rise to the upper end adjacent the outlet. The syringe piston is then depressed sufficiently to force the air out of the syringe. The piston will remain in its partially depressed position so that it is easy for the operator to proceed with injecting the liquid into the patient or infusion device without concern of air being injected.

This procedure cannot be used satisfactorily with the plungerless syringe. While a plungerless syringe can also be oriented with the needle extending upwardly causing the trapped air to rise upwardly, it is very difficult to then carefully move the syringe to a horizontal position and to insert the needle into the patient while holding the plungerless syringe in a partially collapsed position. If the container is squeezed an additional amount during these steps, liquid is, of course, ejected and thus wasted. More importantly, the quantity of fluid being injected into the patient may be unknown and inaccurate. If the collapsing force on the container is relaxed, the container can return to its uncollapsed state, thus drawing contaminated ambient air back into the container through the needle. While the quantity of air initially in a plungerless container is relatively small, and would probably not cause danger to the patient, there is nevertheless a risk involved and hence it is desirable that the air injection risk be eliminated.

The Bane patent, referred to above, discloses a collapsible, bellows-like ampoule wherein, before the needle is inserted, one section of the bellows can be collapsed to expel air. Presumably, this is done while holding the needle upwardly. A button-like plug holds the section collapsed. While this approach would seem to be effective to remove air, the device is not seen in market. Possibly the construction is somewhat expensive.

The above-referenced Lary patent discloses an air vent in a double-walled syringe type container, and refers to ejecting air between a portion of the containers rather than from within the container containing the liquid. It does however, prevent air intake into the inner container.

Thus a need exists for an inexpensive syringe that is practically disposable and that eliminates the air injection problem in an improved manner.

SUMMARY OF THE INVENTION

The present invention satisfies the above-expressed need by providing an inexpensive, blow-molded, collapsible container having a separate chamber which is in communication with the container that traps the air in the chamber. In actuality a blow-fill-seal device such as can be manufactured by Rommelag-Alp machines or perhaps others is contemplated. The chamber is positioned on one side of the container in a location that is generally perpendicular to the direction that the container is squeezed to collapse it. By positioning the syringe with the chamber extending upwardly, the liquid in the chamber will flow by gravity into the container displacing any air in the container into the chamber.

Once the air is in the chamber, an umbilical passage between the chamber and the container is sealed preventing fluid flow therethrough. The umbilical passage is then severed between the point of sealing and the chamber, permanently removing gas from the container regardless of its orientation.

The container is provided with an outlet portion that is conveniently attached to a needle. The needle can be attached to the container during its manufacturing process. However, it is preferable that the liquid outlet for the container be sealed by a suitable plug which is removed and replaced by the needle when the syringe is to be utilized.

The container has a rear wall and a forward wall of similar shape and joined together by a cylindrical band. The rear wall has a surface area greater than the area projected by the cylindrical band. The rear wall is deformable and can be pushed toward the forward wall to eject liquid from the container through the outlet portion. When the rear wall is forced through the cylindrical band, the force necessary to continue is decreased until the rear wall impacts the forward wall, at which time the rear wall is stopped and the ejection of liquid ceases.

The container is formed of material allowing it to snap somewhat into a position with the rear wall adjacent to the forward wall. This snapping action aids a user in knowing when the proper amount of fluid has been ejected.

OBJECTS OF THE INVENTION

Accordingly, it is a primary object of the present invention to provide a syringe adjustable to exclude all gas from within, thereby approximating a 100% liquid environment.

Another object of the present invention is to provide a syringe capable of administering an accurate dose to a patient.

Another further object of the present invention is to provide a syringe of a shape allowing easy ejection of its contents.

Another further object of the present invention is to provide a plungerless syringe which is inexpensive and simple to manufacture and lends itself to mass manufacturing techniques.

Another further object of the present invention is to provide a syringe which can conform to use with either a luer slip, a cannula or a needle.

Another further object of the present invention is to provide a syringe capable of handling a variety of dose sizes.

Viewed from a first vantage point it is an object of this invention to provide a dispenser for ejecting liquid housed within said dispenser and excluding gas from said dispenser, comprising a container having a liquid outlet and a gas outlet, said liquid outlet spaced from said gas outlet, said gas outlet communicating with a chamber through communication means to exclude gas from within said container, and said container having a dispensing means capable of ejecting liquid from within.

Viewed from a second vantage point it is an object of this invention to provide a plungerless syringe comprising a hollow collapsible container made of a material which is sufficiently stiff to maintain its shape but is sufficiently flexible to be manually collapsed by fingers of a user, said container having an outlet through which liquid in said container is ejected upon collapsing said container; and a severable air trap in the form of a small chamber which is in temporary fluid communication with said container through a communication means, said chamber being physically connected to said container in a manner and location such that all air or other gas in said container is displaced into said container; whereby gas is separated from the liquid and prevented from passing through said outlet.

Viewed from a third vantage point it is an object of this invention to provide a method for ejecting liquid from a liquid dispenser while preventing gas within the liquid dispenser from being dispensed with the liquid, the steps including orienting a container and associated chamber to allow gas within the container to move into the associated chamber through a fluid passage, sealing the passage to prevent the gas from reentering the container upon reorienting of the container and associated chamber, positioning the dispenser with an outlet to the container located in a region desired for liquid dispensing, and compressing the wall of the container causing the liquid within the container to be expelled through the outlet.

DESCRIPTION OF PREFERRED EMBODIMENTS

Figure 1A:
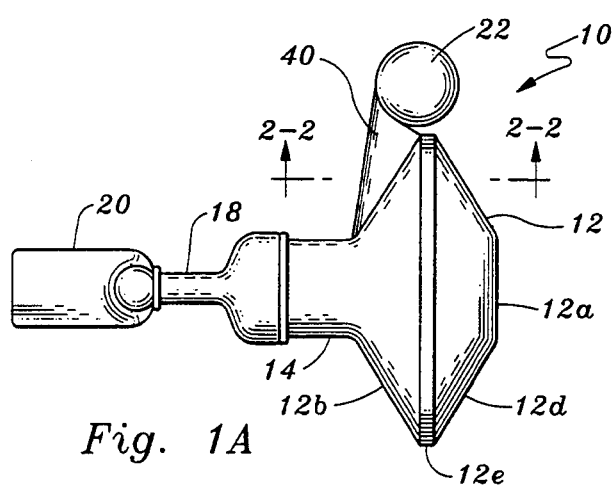
FIG. 1A is a plan view showing the syringe.
Figure 1B:
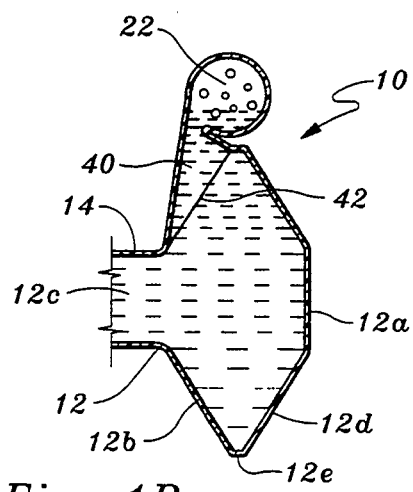
FIG. 1B is a cut away plan view showing inner details of the syringe.

Referring now to the drawings wherein like reference numerals represent like parts throughout, reference numeral 10 refers to a plungerless syringe. The syringe 10 includes a container 12 or a syringe main body, a chamber 22 and an outlet portion 18 spaced from the chamber 22.

Figure 3:
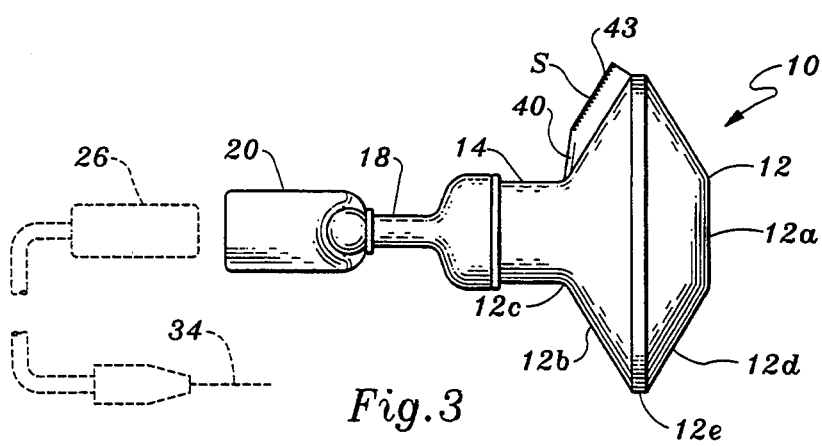
FIG. 3 is a plan view of the syringe with a portion removed.

In essence, the container 12 is a hollow construct having inner and outer surfaces. A forward portion of the container 12 has a central opening 12c which leads into the outlet portion 18 of the syringe 10. The chamber 22 connects to a side of the container 12 through an umbilical passage 40 interposed therebetween. The umbilical passage 40 allows the chamber 22 and the container 12 to be in fluid communication with each other. The outlet portion 18 is connectable to a needle 34, as shown in FIGS. 4B, 4C and 5B, or to a cannula as shown in FIG. 3 for injection of the liquids contained therein into a patient.

More specifically, and referring to FIGS. 1A through 5B, the container 12 is formed from a rear wall 12a, an annular peripheral wall 12d, a central cylindrical band 12e, and a forward wall 12b. The annular peripheral wall 12d and forward wall 12b are frusto-conical in shape with ends of lesser diameter opposite each other, and ends of greater diameter facing each other. Each greater diameter end of the annular peripheral wall 12d and forward wall 12b is connected to opposite ends of the cylindrical band 12e. The rear wall 12a encloses the lesser diameter end of the annular peripheral wall 12d. The lesser diameter end of the forward wall 12b remains open creating the central opening 12c. A neck 14 is attached to the forward wall 12b surrounding the central opening 12c and leads toward the outlet portion 18 of the syringe 10. In one embodiment, shown in FIGS. 4B and 5B, a finger engaging portion 16 is shown circumscribing the neck 14. Finger engaging portion 16 is a thin cylindrical disk fixedly attached to the neck 14. The finger engaging portion 16 allows the user to more effectively utilize the syringe 10.

Figure 4A:
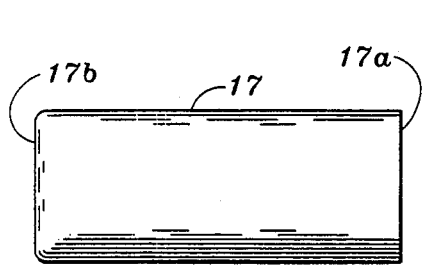
FIG. 4A is a plan view of a cap for the syringe.
Figure 4B:
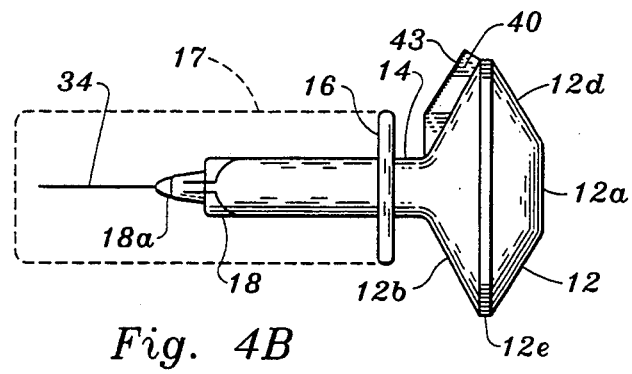
FIG. 4B is a plan view of the syringe with the cap superimposed thereon in phantom.
Figure 4C:
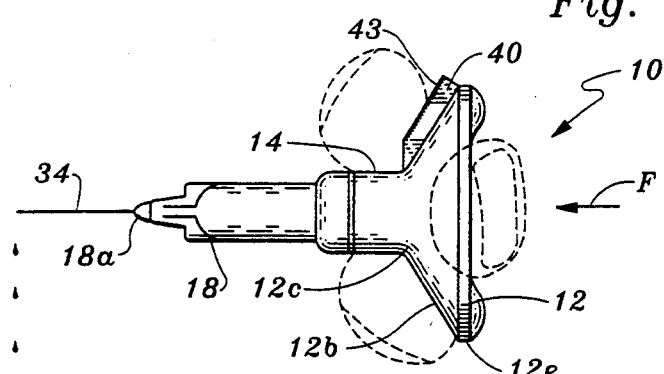
FIG. 4C is a plan view of the syringe being dispensed.
Figure 5A:
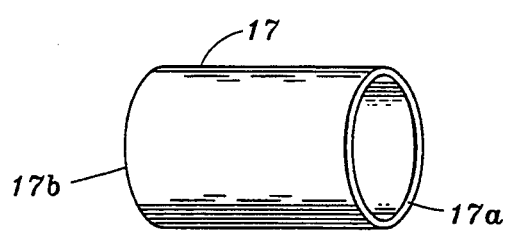
FIG. 5A is an isometric view of a cap for the syringe.
Figure 5B:
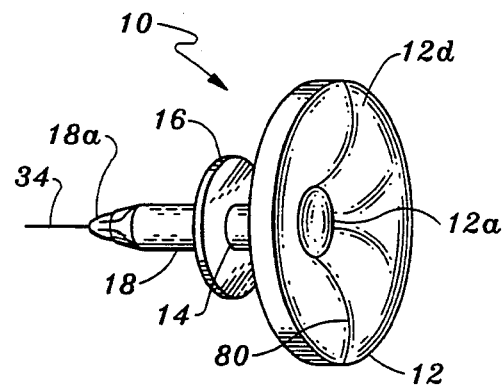
FIG. 5B is an isometric view of the syringe after having dispensed fluid.

A cap 17, shown in FIGS. 4A, 4B and 5A, is provided to cover the needle 34 and keep the outlet 18 in a sterile environment. The cap 17 is a cylindrical hollow construct having a flat end wall 17b enclosing one end and a circular opening 17a on an opposite end. The circular opening 17a is sized to snap over the finger engaging portion 16 securing the cap 17 to the syringe 10.

The chamber 22 is a substantially spherical hollow construct. A portion of the chamber 22 opens into the umbilical passage 40. The umbilical passage 40 has an inside surface 41 (FIGS. 2A and 2B) which is adjacent to the interior of the container 12 and the chamber 22. An orifice 42 in a side of the container 12 provides access to the inside surface 41 of the passage 40. Liquids and gases within the container 12 may freely pass along the inside surface 41 of the umbilical passage 40 into the chamber 22 and vice versa. Along the inside surface 41 of the umbilical passage 40 is formed a seal 43. The seal 43 is one of a variety of connectors capable of sealing off the container 12 from fluid communication with the chamber 22.

Figure 2A:
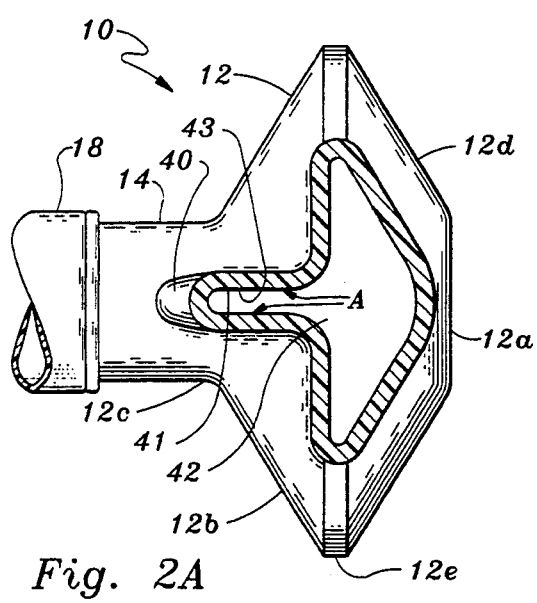
FIG. 2A is a cross-sectional view taken along line 2—2 of FIG. 1A.

One seal 43, shown in FIG. 2A, involves having smooth adjacent inside surfaces 41 of the umbilical passage 40. These surfaces can be connected by application of a welding device on the exterior of the umbilical passage 40. Another alternative method for connection of the inside surfaces 41 of the umbilical passage, shown in FIG. 2A, is to apply adhesive material "A" to the adjacent inside surfaces 41 and compressing the umbilical passage 40 to connect the two inside surfaces 41 together forming the seal 43.

Figure 2B:
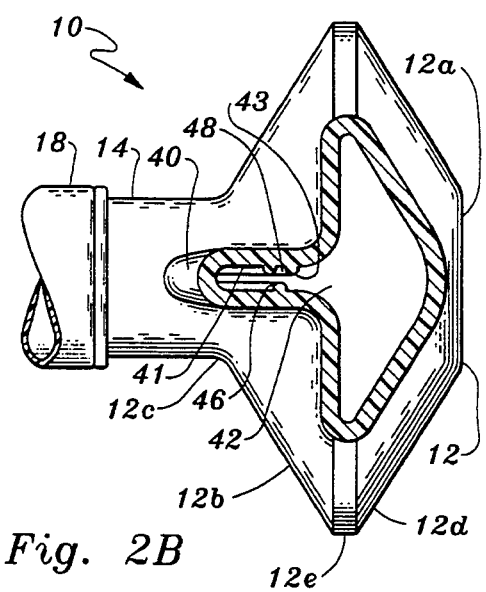
FIG. 2B is a cross-sectional view taken along line 2—2 of FIG. 1A, showing an alternative embodiment of the syringe.

The seal 43 can also be formed, as shown in FIG. 2B, through addition of a tongue 46 on one inside surface 41 and a groove 48 adjacent to the tongue 46 on the opposite inside surface 41. The tongue 46 is sized to fit within the groove 48 such that when compressive forces are applied to the outside of the umbilical passage 40 the seal 43 is formed.

Before utilization of the syringe 10 the outlet portion 18 is fitted with a removable closure 20, shown in FIGS. 1A and 3. The closure 20 is removed before use when a needle 34 or cannula 26 may be connected to the outlet portion 18.

The needle 34 and cannula 26 are formed of a shape similar to those existing in other similar devices readily available in the art. The needle 34 or cannula 26 are connectable to the outlet portion 18 of the syringe 10 in a manner allowing liquids within the container 12 to be ejected through the needle 34 or cannula 26. As shown in FIG. 3, the cannula 26 can connect into another apparatus for injection of the liquid into the patient.

The annular peripheral wall 12d and rear wall 12a are joined together by a linear seam 80, as shown in FIG. 5B, which strategically passes linearly from one side of the cylindrical band 12e along a diameter to an opposite side of the cylindrical band 12e. Typically, the seam 80 occurs in the molding process. The area projected by the cylindrical band 12e when viewed from the rear is less than the total surface area of the rear wall 12a plus the annular peripheral wall 12d.

The container 12 is formed from a material having sufficient flexibility to allow the total surface area of the rear wall 12a and the annular peripheral wall 12d to be compressed so that the total surface area of the rear wall 12a and the annular peripheral wall 12d is less than the cylindrical band 12e, allowing the rear wall 12a to pass through the cylindrical band 12e when a sufficient force F is applied to the rear wall 12a and toward the forward wall 12b.

The seam 80 facilitates buckling of the rear wall 12a and the annular peripheral wall 12d to allow the rear wall 12a to pass through the cylindrical band 12e and continue forward until the annular peripheral wall 12d comes into contact with the forward wall 12b and the rear wall 12a rests over the central opening 12c, as shown in FIGS. 4C and 5B.

Figure 6:
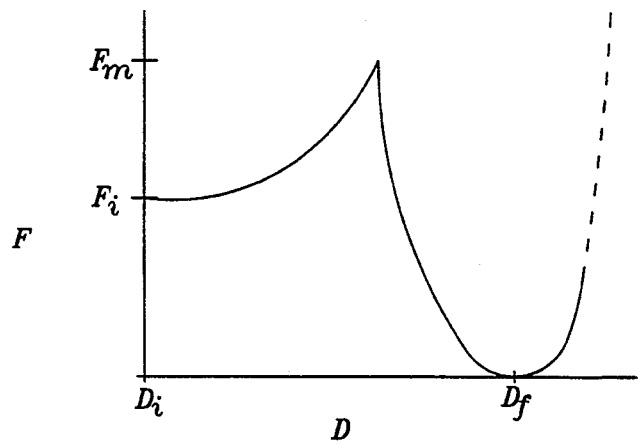
FIG. 6 is a graph expressing force and displacement relationships of the syringe.

Referring now to FIG. 6, the container 12 including the seam 80 is designed to require that an increasing amount of force (from the initial force required, $F_i$) be required to deflect the rear wall 12a more greatly (from the point of no deflection, $D_i$) toward the central opening 12c. This increasing force requirement abruptly changes (when the applied force equals $F_m$, the maximum force required for injection) after the rear wall 12a passes through the cylindrical band 12e, as the rear wall 12a and annular peripheral wall 12d are allowed to expand to their original area on the side of the cylindrical band 12e closer to the central opening 12c. This drop in required force is exhibited until the annular peripheral wall 12d collapses against the forward wall 12b (when rear wall 12a displacement equals $D_f$, the final displacement of the rear wall 12a). The force required to further displace the rear wall 12a then increases sharply because the rear wall 12a is restricted from passing farther into the central opening 12c due to its attachment to the annular peripheral wall 12d which is abutting against forward wall 12b.

The characteristics of this force versus displacement curve of FIG. 6 show that the syringe 10 allows a user to provide a dose to a patient in a fairly predictable amount. An initial force $F_i$ is enough to prohibit the user from accidentally discharging some of the liquid within the container 12 by inadvertently pushing the rear wall 12a slightly. Once the maximum force required $F_m$ is reached, at the point where the rear wall 12a is substantially coplanar with a plane surrounded by the cylindrical band 12e, the force required then drops off rapidly allowing the user to apply only a small force to finish ejecting the remaining liquid. Once the annular peripheral wall 12d impacts the forward wall 12b the position $D_f$ is reached at which point a greater force is required to further depress the rear wall 12a. The user is then signaled by the extra force required for further displacement that the total amount of liquid has been ejected and no further force need be applied to the rear wall 12a of the container 12.

In use and operation, the syringe 10 is to be evacuated of any air contained within the container 12 through the following process. First, the container 12 is oriented with the chamber 22 above the container 12 in elevation. Any air within the container 12 then floats to the top as gravity draws liquid within the chamber 22 and container 12 downward. Vibration (tapping) may assist this step. Once all of the gas has passed upward through the umbilical passage 40 into the chamber 22, the umbilical passage 40 may then be sealed using the seal 43. The chamber 22 may then be severed from the container 12 by either cutting the umbilical passage 40 between the seal 43 and the chamber 22 with a cutting tool or by tearing the umbilical passage 40 along a score line S formed around the umbilical passage 40 providing a guide for manual tearing away of the chamber 22. The device also lends itself to air (or gas) sequestration at the site of fabrication and fluid introduction using an automated process.

Once the chamber 22 has been removed from the container 12, the syringe 10 is ready for use on a patient without risk that air will be injected therefrom.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A plungerless syringe for ejecting liquid housed within said syringe and excluding gas from said syringe, comprising in combination:

a syringe main body having a liquid outlet and a gas outlet, said liquid outlet spaced from said gas outlet, said gas outlet communicating with a chamber through sealable communication means, said sealable communication means connecting said chamber to said syringe main body with a passage on an interior thereof, such that when said syringe main body and said chamber are oriented in a manner causing gas to migrate from said syringe main body to said chamber, said passage is sealable to permanently exclude gas from within said syringe main body, and said syringe main body having a dispensing means capable of ejecting liquid from within.

2. The syringe of claim 1 wherein said dispensing means is said syringe main body being formed with at least one wall which moves from a first position to a second position, said first position defining a liquid retaining position whereupon the liquid remains stored within said syringe main body, and said second position defining a liquid ejected position whereupon the liquid has been expelled from said syringe;

whereby when said one wall moves from said first position to said second position liquid is ejected from within said syringe main body.

3. The syringe of claim 1 wherein said sealable communication means includes sealing means for sealing said sealable communication means shut, whereby gas or liquid is prohibited from passing through said sealable communication means when said sealing means is utilized.

4. The syringe of claim 3 wherein said sealable communication means is said passage having a hollow interior interfacing with both said syringe main body and said chamber on opposite ends thereof.

5. The syringe of claim 4 wherein a chamber separation means is provided capable of separating said chamber from fluid communication with said syringe main body through severance of said passage between said sealing means and said chamber.

6. The syringe of claim 5 wherein said sealing means is the interior wall of said passage formed from a material amenable to localized interconnection through a welding means;

whereby when compressive force is applied to said passage along with said welding means, opposite sides of said inner wall are welded together prohibiting fluid or gas from passing therebeyond.

7. The syringe of claim 5 wherein said chamber separation means is said passage formed from a material amenable to severance by a cutting tool.

8. The syringe of claim 5 wherein said dispensing means is said syringe main body being formed with at least one wall which moves from a first position to a second position, said first position defining a liquid retaining position whereupon the liquid remains stored within said syringe main body, and said second position defining a liquid ejected position whereupon the liquid has been expelled from said syringe;

whereby when said one wall moves from said first position to said second position, liquid is ejected from within said syringe main body.

9. A dispenser for ejecting liquid housed within said dispenser and excluding gas from said dispenser, comprising in combination:

a container having a liquid outlet and a gas outlet, said liquid outlet spaced from said gas outlet, said gas outlet communicating with a chamber through sealable communication means to permanently exclude gas from within said container, and said container having a dispensing means capable of ejecting liquid from within, wherein said sealable communication means includes sealing means for sealing said sealable communication means shut, whereby, gas or liquid is prohibited from passing through said sealable communication means when said sealing means is utilized, wherein said sealable communication means is an umbilical passage having a hollow interior interfacing, with both said container and said chamber on opposite ends thereof, wherein a chamber separation means is provided capable of separating said chamber from fluid communication with said container through severance of said umbilical passage between said sealing means and said chamber, and wherein said sealing means is a tongue fixedly attached to one side of an interior wall of said umbilical passage spanning the width of said umbilical passage and oriented non-parallel to an axis penetrating said ends of said umbilical passage; and a groove complemental to said tongue and formed to a second side of said interior wall of said umbilical passage opposite said tongue, whereby when compressive force is applied to said umbilical passage said tongue locks into said groove prohibiting fluid or gas from passing therebeyond.

10. A dispenser for ejecting liquid housed within said dispenser and excluding gas from said dispenser, comprising in combination:
   a container having a liquid outlet and a gas outlet, said liquid outlet spaced from said gas outlet,
   said gas outlet communicating with a chamber through sealable communication means to permanently exclude gas from within said container, and
   said container having a dispensing means capable of ejecting liquid from within,
   wherein said sealable communication means includes sealing means for sealing said sealable communication means shut, whereby gas or liquid is prohibited from passing through said sealable communication means when said sealing means is utilized,
   wherein said sealable communication means is an umbilical passage having a hollow interior interfacing with both said container and said chamber on opposite ends thereof,
   wherein a chamber separation means is provided capable of separating said chamber from fluid communication with said container through severance of said umbilical passage between said sealing means and said chamber, and
   wherein said sealing means is an adhesive coating applied to opposite sides of an interior wall of said umbilical passage spanning the width of said umbilical passage;
   whereby when compressive force is applied to said umbilical passage said opposite sides of said interior walls stick together prohibiting fluid or gas from passing therebeyond.

11. A dispenser for ejecting liquid housed within said dispenser and excluding gas from said dispenser, comprising in combination:
   a container having a liquid outlet and a gas outlet, said liquid outlet spaced from said gas outlet,
   said gas outlet communicating with a chamber through sealable communication means to permanently exclude gas from within said container, and
   said container having a dispensing means capable of ejecting liquid from within,
   wherein said sealable communication means includes sealing means for sealing said sealable communication means shut, whereby gas or liquid is prohibited from passing through said sealable communication means when said sealing means is utilized,
   wherein said sealable communication means is an umbilical passage having a hollow interior interfacing with both said container and said chamber on opposite ends thereof,
   wherein a chamber separation means is provided capable of separating said chamber from fluid communication with said container through severance of said umbilical passage between said sealing means and said chamber, and
   wherein said chamber separation means is a score line formed peripherally around said umbilical passage of sufficient depth to allow tearing away of said chamber and said umbilical passage above said groove, from said container and said umbilical passage below said groove.

12. A dispenser for ejecting liquid housed within said dispenser and excluding gas from said dispenser, comprising in combination:
   a container having a liquid outlet and a gas outlet, said liquid outlet spaced from said gas outlet,
   said gas outlet communicating with a chamber through sealable communication means to permanently exclude gas from within said container, and
   said container having a dispensing means capable of ejecting liquid from within,
   wherein said sealable communication means includes sealing means for sealing said sealable communication means shut, whereby gas or liquid is prohibited from passing through said sealable communication means when said sealing means is utilized,
   wherein said sealable communication means is an umbilical passage having a hollow interior interfacing with both said container and said chamber on opposite ends thereof,
   wherein a chamber separation means is provided capable of separating said chamber from fluid communication with said container through severance of said umbilical passage between said sealing means and said chamber, and
   wherein said dispensing means is said container being formed with at least one wall which moves from a first position to a second position,
   said first position defining a liquid retaining position whereupon the liquid remains stored within said container,
   and said second position defining a liquid ejected position whereupon the liquid has been expelled from said dispenser;
   whereby when said one wall moves from said first position to said second position, liquid is ejected from within said container, and
   wherein said one wall is of a greater surface area than the maximum area projected by a peripheral wall surrounding said one wall, and said peripheral wall is located between said first position and said second position,
   whereby increasing force is required to move said one wall from said first position toward said second position until said one wall is compressed in area enough to pass through and does pass through said peripheral wall, and then decreasing force is required to move said one wall toward said second position, thereby assisting a user of said dispenser in moving said one wall precisely a desired amount.

13. A plungerless syringe comprising a hollow, collapsible container made of a material which is sufficiently stiff to maintain its shape but is sufficiently flexible to be manually collapsed by fingers of a user, said container having an outlet through which liquid in said container is ejected upon collapsing said container; and
   a severable air trap in the form of a small chamber which is in temporary fluid communication with said container through a sealable communication means, said chamber being physically connected to said container with a passage such that all air or other gas in said container is displaced into said chamber;
   whereby gas is separated from the liquid and prevented from passing through said outlet.

14. The syringe of claim 13 wherein said sealable communication means is said passage having a hollow interior interfacing with both said container and said chamber on opposite ends thereof.

15. The syringe of claim 14 wherein said passage includes sealing means and severance means between said sealing means and said chamber;

whereby said passage can be blocked and said chamber can be removed from said syringe, leaving said container of said syringe without any gas therein.

16. The syringe of claim 15 wherein said sealing means is the interior wall of said passage formed from a material amenable to localized interconnection through a welding process;
  whereby when compressive force is applied to said passage along with a welding instrument, opposite sides of said inner wall are welded together prohibiting fluid or gas from passing therebeyond.

17. The syringe of claim 15 wherein said severance means is said passage formed from a material amenable to severance by a cutting tool.

18. A plungerless syringe comprising a hollow, collapsible container made of a material which is sufficiently stiff to maintain its shape but is sufficiently flexible to be manually collapsed by fingers of a user, said container having an outlet through which liquid in said container is ejected upon collapsing said container; and
  a severable air trap in the form of a small chamber which is in temporary fluid communication with said container through a communication means, said chamber being physically connected to said container in a manner and location such that all air or other gas in said container is displaced into said chamber;
  whereby gas is separated from the liquid and prevented from passing through said outlet,
  wherein said communication means is an umbilical passage having a hollow interior interfacing with both said container and said chamber on opposite ends thereof,
  wherein said umbilical passage includes sealing means and severance means between said sealing means and said chamber;
  whereby said umbilical passage can be blocked and said chamber can be removed from said syringe, leaving said container of said syringe without any gas therein, and
  wherein said sealing means is a tongue fixedly attached to one side of an interior wall of said umbilical passage spanning the width of said umbilical passage and oriented non-parallel to an axis penetrating said ends of said umbilical passage;
  and a groove complemental to said tongue and formed to a second side of said interior wall of said umbilical passage opposite said tongue,
  whereby when compressive force is applied to said umbilical passage said tongue locks into said groove prohibiting fluid or gas from passing therebeyond.

19. A plungerless syringe comprising a hollow, collapsible container made of a material which is sufficiently stiff to maintain its shape but is sufficiently flexible to be manually collapsed by fingers of a user, said container having an outlet through which liquid in said container is ejected upon collapsing said container; and
  a severable air trap in the form of a small chamber which is in temporary fluid communication with said container through a communication means, said chamber being physically connected to said container in a manner and location such that all air or other gas in said container is displaced into said chamber;
  whereby gas is separated from the liquid and prevented from passing through said outlet,
  wherein said communication means is an umbilical passage having a hollow interior interfacing with both said container and said chamber on opposite ends thereof,
  wherein said umbilical passage includes sealing means and severance means between said sealing means and said chamber;
  whereby said umbilical passage can be blocked and said chamber can be removed from said syringe, leaving said container of said syringe without any gas therein, and
  wherein said sealing means in an adhesive coating applied to opposite sides of an interior wall of said umbilical passage spanning the width of said umbilical passage;
  whereby when compressive force is applied to said umbilical passage said opposite sides of said interior walls stick together prohibiting fluid or gas from passing therebeyond.

20. A plungerless syringe comprising a hollow, collapsible container made of a material which is sufficiently stiff to maintain its shape but is sufficiently flexible to be manually collapsed by fingers of a user, said container having an outlet through which liquid in said container is ejected upon collapsing said container; and
  a severable air trap in the form of a small chamber which is in temporary fluid communication with said container through a communication means, said chamber being physically connected to said container in a manner and location such that all air or other gas in said container is displaced into said chamber;
  whereby gas is separated from the liquid and prevented from passing through said outlet,
  wherein said communication means is an umbilical passage having a hollow interior interfacing with both said container and said chamber on opposite ends thereof,
  wherein said umbilical passage includes sealing means and severance means between said sealing means and said chamber;
  whereby said umbilical passage can be blocked and said chamber can be removed from said syringe, leaving said container of said syringe without any gas therein, and
  wherein said severance means is a score line formed peripherally around said umbilical passage of sufficient depth to allow tearing away of said chamber and said umbilical passage above a groove, from said container and said umbilical passage below said groove.

21. A plungerless syringe which prevents gas from being dispensed with the liquid, said syringe being the product of the steps of:
  providing the syringe with a liquid storage container having both a liquid outlet and a gas outlet spaced from the liquid outlet and having a gas outlet seal on the container at the gas outlet, the seal preventing fluid from passing therebeyond,
  filling the container with liquid,
  sealing the container from fluid communication outside said container,
  orienting the syringe to purge gas through the gas outlet, and
  sealing the gas outlet.

22. A method for manufacturing and filling a plungerless syringe with liquid and precluding gas from being dispensed therefrom, the steps including:

forming the syringe with a container having a liquid outlet and a chamber communicating with the container by means of a gas outlet spaced from the liquid outlet, filling the container with liquid, sealing the syringe from access to further liquid, orienting the container and associated chamber to allow gas within the container to move into the associated chamber through the gas outlet, and sealing the passage to prevent the gas from reentering the container upon reorienting of the container and associated chamber.

23. The method of claim 22 wherein severing of the gas outlet occurs between a sealing location and a chamber location after said sealing step, whereby the chamber and included gas are removed from the dispenser.

24. The method of claim 22 wherein said sealing step includes connecting opposite walls of the gas outlet by inserting a tongue on one wall into a complementally formed groove on an opposite wall;

whereby the gas outlet is sealed from passage of liquid therethrough.

25. The method of claim 22 wherein said sealing step includes steps of applying adhesive to opposite walls of the gas outlet, and compressing opposite walls of the gas outlet together causing the opposite walls to stick together.

26. The method of claim 22 wherein said sealing step includes steps of:

compressing opposite walls of the gas outlet together and welding the two opposite walls together causing a seal between the opposite walls.

27. The method of claim 22 wherein said compressing step is followed by stopping the compression of the wall of the container through abutment of the wall with an opposite container wall, whereby the container is restricted from compression beyond a desired amount.

28. The method of claim 27 wherein said compressing step includes:

applying an initial force to begin compression of the of the wall of the container, increasing the force applied up to a maximum force required to compress the wall within a peripheral wall of the container, and decreasing the force applied while the wall of the container approaches the abutment position of the container wall against the opposite container wall attained at said stopping step, whereby an increasing force is required to initiate ejection of the liquid through the liquid outlet and decreasing force is required to finish ejection of the liquid through the liquid outlet, thereby aiding a user in ejecting exactly the amount of liquid desired.

29. The method of claim 28, including the further step of severing the chamber from the container while maintaining a seal on said container at said gas outlet so as to prevent the liquid from escaping therefrom.

30. A liquid ejecting plungerless syringe comprising in combination:

a hollow collapsible container containing liquid and sealed from fluid communication outside said container;

a liquid outlet in fluid communication with said container;

a gas outlet spaced from said liquid outlet; and a gas outlet seal disposed on said gas outlet, which prevents fluid from passing therebeyond.

31. A plungerless syringe for ejecting gas-less liquid housed within said syringe, said syringe being the product of the steps of:

forming said syringe with a container having both a liquid outlet and a gas outlet which is spaced from said liquid outlet;

a chamber communicating with said container by means of said gas outlet interposed between said container and said chamber;

filling said container with fluid;

orienting said container and said chamber to allow gas within said container to move into said chamber through said gas outlet; and sealing said gas outlet to prevent gas from reentering said container.

* * * * *